US005800821A

United States Patent [19]
Acheson et al.

[11] Patent Number: 5,800,821
[45] Date of Patent: Sep. 1, 1998

[54] BACTERIAL SPORES AS A HEAT STABLE VACCINE DELIVERY SYSTEM

[75] Inventors: David W. K. Acheson, Norwood; Abraham L. Sonenshein, Brookline; Gerald T. Keusch, Lexington, all of Mass.

[73] Assignees: New England Medical Center Hospitals, Inc., Boston; Trustees of Tufts College, Medford, both of Mass.

[21] Appl. No.: 402,347

[22] Filed: Mar. 10, 1995

[51] Int. Cl.$^6$ ................................................ A61K 39/02
[52] U.S. Cl. ........................ 424/200.1; 424/93.41; 424/93.46; 424/234.1; 424/246.1; 424/247.1
[58] Field of Search ........................ 424/246.1, 200.1, 424/247.1, 234.1, 93.46, 93.41

[56] References Cited

U.S. PATENT DOCUMENTS 5,223,409  6/1993  Lander et al. ........................ 435/69.7

FOREIGN PATENT DOCUMENTS 9402170  6/1996  WIPO .

OTHER PUBLICATIONS

Al–Dabbass, A.H. et al., "Immunizing Activity of Oil Adjuvant Attenuated Spore Vaccine of Bacillus anthracis in Sheep", 1986, *J. Vet. Med. B.*, 33:340–45.
Andrew, M.E. et al., "Vaccinia Virus Recombinants Expressing the SA11 Rotavirus VP7 Glycoprotein Gene Induce Serotype–Specific Neutralizing Antibodies", 1987, *J. Virology*, 61(4):1054–60.
Bhatnagar, R.N. et al., "Fluctuations in the Levels of Complement Activities, Conglutinin, Immunoconglutinin and Heterohaemagglutinin in the Sera of Sheep Vaccinated with Anthrax Spore Vaccine and Challenged with Bacillus Anthracis", 1988, *Indian Vet. J.*, 65:959–64.
Cheyne, J. "Vaccine Delivery Management", 1989, *Rev. Infectious Diseases*, 1989, 2(3):S617–22.
Eldridge, J.H. et al., "Biodegradable Microspheres: Vaccine Delivery System for Oral Immunization", 1989, *Current Topics in Microbiol. and Immunol.*, 146:59–66.
Formal, S.B. et al., "Construction of a Potential Bivalent Vaccine Strain: Introduction of Shigella sonnei Form I Antigen Genes into the galE Salmonella typhi Ty21a Typhoid Vaccine Strain", *Infection and Immunity*, 34(3):746–50.
Forrest, B.D. et al., "Immunogenicity of a Candidate Live Oral Typhoid/Cholera Hybrid Vaccine in Humans", 1989, *J. Infectious Diseases*, 159(1):145–46.
Foster, S.J. et al., "Pulling the Trigger: the Mechanism of Bacterial Spore Germination", 1990, *Molecular Microbiology*, 4(1):137–41.
Hemiliä, H., et al., "Production of Diphheria Toxin CRM228 in B. subtilis",1989 *FEMS Microbiol. Letters*, 65:193–98.
Hilleman, M., "Improving the Heat Stability of Vaccines: Problems, Needs, and Approaches", 1989, *Reviews of of Infectious Diseases*, 2(3)S613–16.

Isberg, R.R. et al., "Identification of Invasin: A Protein That Allows Enteric Bacteria to Penetrate Cultured Mammalian Cells", 1987, *Cell*, 50:769–78.
Isberg, R.R. et al., "Multiple $\beta_1$ Chain Integrins Are Receptors for Invasin, a Protein That Promotes Bacterial Penetration into Mammalian Cells", 1990, *Cell*, 60:861–71.
Ivins, B.E. et al., "Cloning and Expression of the Bacillus anthracis Protective Antigen Gene in Bacillus subtilis", 1986, *Infection and Immunity*, 54(2):537–42.
Ivins, B.E. et al., "Immunization against Anthrax with Aromatic Compound–Dependent (Aro$^-$) Mutants of Bacillus anthracis and with Recombinant strains of Bacillu subtilis That Produce Anthrax Protective Antigen", 1990, 58(2):303–308.
Jaiswal, T.N. et al., "Potency Testing of Anthrax Spore Vaccine (Living) in Guinea Pigs", 1979, *Indian Vet. J.*, 56:199–201.
Kotloff, K.L. et al., "Safety, Immunogenicity, and Efficacy in Monkeys and Humans of Invasive Escherichia coli K–12 Hybrid Vaccine Candidates Expressing Shigella flexneri 2a Somatic Antigen", 1992, *Infection and Immunity*, 60(6):2218–24.
Levine, M.M. et al., "Safety, Immunogenicity, and Efficacy of Recombinant Live Oral Cholera Vaccines, CVD 103 and CVD 103–HgR", 1988, *The Lancet: Saturday Aug. 27, 1988*, 2(8609):467–70.
Little, S.F. et al., "Comparative Efficacy of Bacillus anthracis Live Spore Vaccine and Protective Antigen Vaccine Against Anthrax in the Guinea Pig", 1986, *Infection and Immunity*, 52(2):509–12.
Migasena, S. et al., "Preliminary Assessment of the Safety and Immunogenicity of Live Oral Cholera Vaccine Strain CVD 103–HgR in Healthy Thai Adults", 1989, *Infection and Immunity*, 57(11):3261–64.
Mwangi, D.M. et al., "Immunosuppression in Caprine Trypanosomiasis: Effects of Acute Trypanosoma Congolense Infection on Antibody Response to Anthrax Spore Vaccine", 1990, *Trop. Anim. Hlth. Prod.*, 22:95–100.
Priest, F., "Systematics and Ecology of Bacillus", In *Bacillus subtilis and other Gram–positive Bacteria*, Sonenshein et al., (eds) Am. Society for Microbiology, Washington, DC, Ch. 1, pp. 3–16, (1993).
Robbins, A., "Progress Towards Vaccines We Need and Do Not Have", 1990, *The Lancet*, 335(8703):1436–38.

(List continued on next page.)

*Primary Examiner*—James C. Housel
*Assistant Examiner*—Jennifer Shaver
*Attorney, Agent, or Firm*—Fish & Richardson, P.C.

[57] ABSTRACT

A method of stimulating a vertebrate animal to produce an immune response to at least one antigen is described. The method includes genetically engineering a bacterial cell with DNA encoding at least one antigen and inducing the bacterial cell to sporulate, then orally administering the bacterial spores to an animal. The bacterial spores germinate in the gastrointestinal tract of the animal and express the antigen so that it comes into contact with the animal's immune system and elicits an immune response.

9 Claims, 3 Drawing Sheets

OTHER PUBLICATIONS

Saris, P. et al., "Production and Secretion of Pertussis Toxin Subunits in *Bacillus subtillis*", 1990, *FEMS Microbiol. Letters*, 68:143–48.

Setlow "Spore Structural Proteins", *Bacillus subtilis* and Other Gram–positive Bacteria, Sonenshein et al., (eds.), *Amer. Society for Microbiology, Washington, D.C.*, Ch. 55, pp. 801–809, (1993).

Sotoodehnia, A. et al., "The Comparison of Two Anthrax Spore Vaccines Prepared with Sterne 34F2 and Native C5 Strains in Sheep and Goats in Iran", 1984, *Arch. Inst. Razi*, 34:51–54.

Stott, E.J. et al., "Immune and Histopathological Responses in Animals Vaccinated with Recombinant Vaccinia Viruses That Express Individual Genes of Human Respiratory Syncytial Virus", 1987, *J. Virology*, 61:3855–61.

Su, G.F. et al., "Construction of Stable LamB–Shiga Toxin B Subunit Hybrids: Analysis of Expression in *Salmonella typhimurium* aroA Strains and Stimulation of B Subunit–Specific Mucosal and Serum Antibody Responses", 1992, *Infection and Immunity*, 60(8):3345–59.

Tacket, C.O. et al., "Safety, Immunogenicity, and Efficacy Against Cholera Challenge in Humans of a Typhoid–Cholera Hybrid Vaccine Derived From Salmonella Typhi Ty21a", 1990, *Infection and Immunity*, 58(6):1620–27.

Taira, S. et al., "Production of Pneumolysin, a Pneumococcal Toxin in *Bacillus subtilis*", 1989, *Gene*, 77:211–18.

Welkos, S.L. et al., "Comparative Safety and Efficacy Against *Bacillus anthracis* of Protective Antigen and Live Vaccines in Mice", 1988, *Microbial Pathogenesis*, 5:127–39.

Ivins et al, Nov. 1986. Infection & Immunity. 54(2): 537–542.

Labruyere et al. 1990. Molecular Microbiol. 4(7):1111–1117.

BACTERIAL SPORES AS A HEAT STABLE VACCINE DELIVERY SYSTEM

Statement as to Federally Sponsored Research

This invention was made with Government support under NIAID grant #16242 awarded by the Public Health Service. The Government has certain rights in the invention.

BACKGROUND OF THE INVENTION

The field of the invention is vaccination and immunization.

Immunization programs have been responsible for both significant increases in life expectancy and decreases in morbidity over the last 50 years. A 1986 symposium on vaccine development and utilization challenged molecular biologists, immunologists, and manufacturers to design and adapt vaccines to make them cheaper, safer, more immunogenic, more stable, and easier to deliver (International symposium on vaccine development and utilization, Rev. Infect. Dis., 1989, 11:S491–S667). Recently there has been even greater awareness by the Federal Government of the need for vaccine development (Cohen, *Science*, 1993, 259:1528–29; *NIH Guide*, 1993, 22:(28)). The establishment of the Children's Vaccine Initiative (CVI) with the help of WHO, UNICEF, the United Nations Development Project, and the Rockefeller Foundation underscores the global nature of the recent initiatives.

The various agencies and groups involved in vaccine development, including the CVI, have stated a number of priorities, including development of the "ideal vaccine." A precise definition of the ideal vaccine may not have universal consensus, but the following characteristics are generally agreed to be important: 1) successful immunization with a single dose by the oral route, 2) high heat stability, 3) multicomponent character, 4) long-lasting protection, 5) simplicity of administration, and 6) affordability.

One of the greatest technical obstacles to universal immunization is lack of heat stability of many vaccines (Bart, *Rev. Infect. Dis.*, 1989, 11:S491–92, Hilleman, *Rev. Infect. Dis.*, 1989, 11:S613–16). There are many problems inhibiting the development of heat stable vaccine systems. For example, biologics made of organic polymers must maintain their primary and secondary structures in order to retain their ability to induce specific protective immune responses (Hilleman, 1989, supra). Loss of hydrogen bonding and glycosyl groups may have significant effects on folding. Oxygen and oxidants destabilize proteins by their action on the sulfhydryl group of cysteine, causing crosslinking and distortion. Oxidation of the sulfur in methionine to sulfoxide causes the hydrophobic residue to become hydrophilic, resulting in distortion of the secondary structure of a protein. All of these adverse effects are promoted by increases in temperature. Other problems in producing heat-stable vaccines include economics (in terms of manufacturers' development cost:profit ratios) and the costs associated with field testing. The expense and difficulty of developing heat-stable vaccine delivery systems must be weighed against the cost and difficulty of providing and maintaining an adequate cold chain from the manufacturer to the final user.

Although there have been major advances in establishing adequate cold chains, e.g., the incorporation of monitoring systems to detect breaks in the chain. (Cheyne, *Rev. Infect. Dis.*, 1989, 11:S617–22), cold chain purchase and maintenance is still a significant expense and failures may be overlooked or not reported. Even with an adequate cold chain, many vaccines, such as oral poliovirus vaccine and BCG, will only survive at 2°–8° C. for approximately one year (Cheyne, 1989, supra). This can be a severe limitation on the time available for distribution of vaccines from the manufacturer to the recipient.

SUMMARY OF THE INVENTION

We have discovered an inexpensive method to make heat-stable, long-lived, oral vaccines using a recombinant live organism.

Accordingly, the invention features a method of stimulating or inducing a vertebrate animal to produce an immune response to one or more antigens (immunize) by transforming or genetically engineering a bacterial cell which is capable of forming spores with heterologous DNA. This DNA encodes one or more antigens which are expressed individually or as fusion proteins, and it may also encode other proteins. The engineered (recombinant) bacterial cells are then induced to form spores using methods known in the art, and the spores are orally administered to the animal to be immunized. The antigen or antigens encoded by the heterologous DNA are expressed by the ingested bacterial cell or spore and come into contact with the animal's immune system via the intestinal mucosa.

By "immunize" or "induce an immune response" is meant production of antibodies or cell-mediated immune responses by the animal so immunized to protect it from future infection by a pathogenic agent.

In one embodiment, the antigen is expressed on the surface of the orally administered spore, so that the antigen comes into contact with the immune system (generally, lymphocytes in the blood or mucosa) of the animal upon ingestion. The antigen is expressed on the spore surface, individually or as a fusion protein, preferably with a spore coat protein. If the antigen is expressed on the surface of the spore, it can exert its immunogenic effects without germination of the spore. For example, an immune response can be elicited from the animal if the antigens contact or are taken up by cells in the mucosa, such as M cells.

In an alternate embodiment, the spores germinate in the host animal after ingestion, and replicate as vegetative bacterial cells, producing the recombinantly encoded antigen(s) by expressing the foreign (heterologous) DNA. Depending on how the DNA was engineered to interact with the bacterial vector, the expressed antigen can be secreted by the bacterial cells or transported to the surface of the cell and integrated there (e.g., via a fusion construction with a cell wall protein). In either alternative, the antigen comes into contact with the cells of the host animal and elicits an immune response. A "vector" is the carrier of the antigen-encoding DNA, and can mean either the bacterial cell itself, or the plasmid into which the desired DNA is inserted prior to its introduction into a bacterium.

In preferred embodiments, other DNA, e.g., encoding cell adherence proteins, may be introduced into and expressed by vector bacteria in addition to the antigen-encoding DNA. The antigen and adherence proteins may be expressed as fusion proteins with endogenous bacterial cell wall or spore coat associated proteins, or any other desired proteins. By "adherence protein" is meant one which allows the cell in which it is expressed to adhere to another cell, preferably a vertebrate animal cell, more preferably a mammalian cell. Examples of such proteins which may be expressed by the bacteria used in the invention are Invasin (Inv) from *Yersinia enterocolitica* or Colonization Factor Antigens (CFAs) from enterotoxigenic *E. coli*. Inv, CFAs or other adherence proteins may be both protective antigens and a mechanism to allow colonization of the vector strain in the intestinal tract. These proteins will generally be expressed so that they are at least partially exposed on the surface of the spore or vegetative bacterial cell to ensure that they have access to binding sites on animal cells.

In preferred embodiments, the genetically engineered spores may be treated prior to oral administration to initiate germination. This is also known as "activation" and can be achieved by aging or more preferably by heat treatment and exposure to germinants, e.g., applying heat shock and L-alanine or a mixture of glucose, fructose, asparagine, and KCl (GFAK). This activation allows spores to retain surface proteins, but makes them more permeable to specific germinants, allowing them to grow into vegetative cells more efficiently. A preferred method of activating spores prior to oral administration is to suspend them in a hot broth or water, then cool the suspension to a suitable temperature prior to administration to the animal, e.g., a human.

The spore or resultant vegetative cell of the invention preferably has a residence time in the digestive tract of the animal of at least one day, more preferably at least two to ten days, or possibly permanent colonization.

A preferred genus of bacteria for use as the vector for the antigen-encoding DNA of the invention is Bacillus. However, many other genera are suitable, including the genera Clostridium, Actinomycetes, Streptomyces, Nocardia, or any spore forming bacterium. Implementation of the invention in some bacteria (e.g., human pathogens) may require the use of mutants which lack expression of toxins or other pathogenic characteristics.

In another embodiment of the invention, vegetative bacterial cells are genetically altered by introduction of heterologous DNA encoding one or more antigens and possibly other proteins, and these cells are orally administered to a vertebrate animal. The administered bacterial cells express the antigen and any other proteins encoded by the foreign DNA. The expressed antigens are exposed to the enteric cells of the animal which ingested the bacteria, and elicit an immune response in that animal.

In preferred embodiments, the encoded antigen is expressed on the surface of the ingested bacterial cells, or secreted by the bacterial cells so that the antigen comes into contact with the cells of the host animal and elicits an immune response.

In another embodiment, the heterologous DNA also encodes an adherence protein, e.g., Invasin, which is expressed on the surface of the bacterial cell so that the bacterial cells can adhere to the cells of the animal which ingested them.

Alternatively, a DNA encoding a heterologous antigen can be expressed on the surface of a recombinant bacterial spore which is suitable for ingestion and able to germinate following ingestion. Upon ingestion and germination, the same or a different heterologous antigen can be expressed on the surface of or secreted by the resulting vegetative bacteria. This embodiment has the advantage of exposing the animal to the desired antigen immediately upon ingestion, and continuing antigenic exposure through bacterial germination and vegetative cell growth.

The invention is built around the concept of using bacterial spores as an orally administered vector either for direct presentation of antigens, or for transport of the DNA encoding specific antigens. Using bacterial spores offers a different, conceptually simple, and practical solution to vaccine antigen delivery. It allows ambient temperature vaccine storage in any climate, and oral administration which is both easy and safe. This type of vaccine will be simple and inexpensive to produce, and will have a prolonged shelf life. There are clear and undisputed advantages of oral administration in terms of ease, safety, cost, and acceptability.

Other features and advantages of the invention will be apparent from the following description of the preferred embodiments thereof, and from the claims.

DETAILED DESCRIPTION

Figure 1:
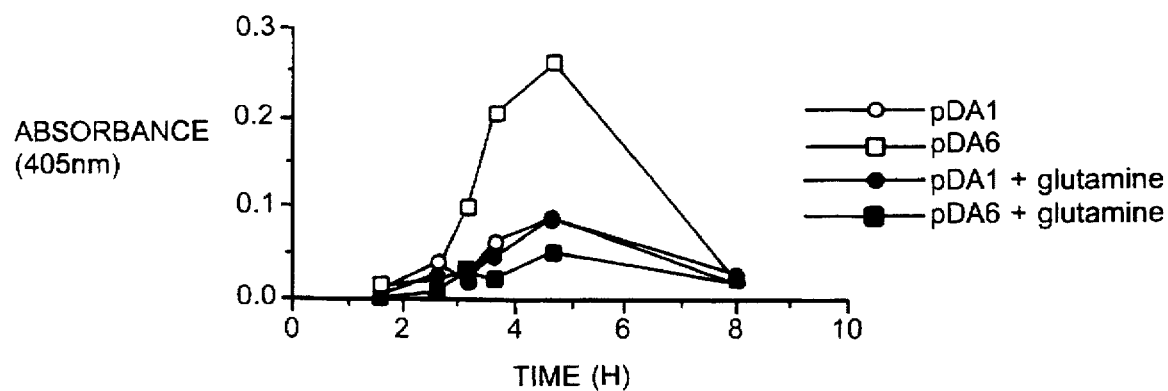
FIG. 1 is a graph showing SLT-I B subunit expression in B. subtilis using the SPAC promoter (pDA1) or glutamine synthetase promoter (pDA6) with and without added glutamine in the culture medium (L. broth). The B subunit in culture supernatants was measured by ELISA using a B subunit specific monoclonal antibody as the capture molecule, and is given as absorbance units. Cultures reached stationary phase at 4-5 hours.
Figure 3:
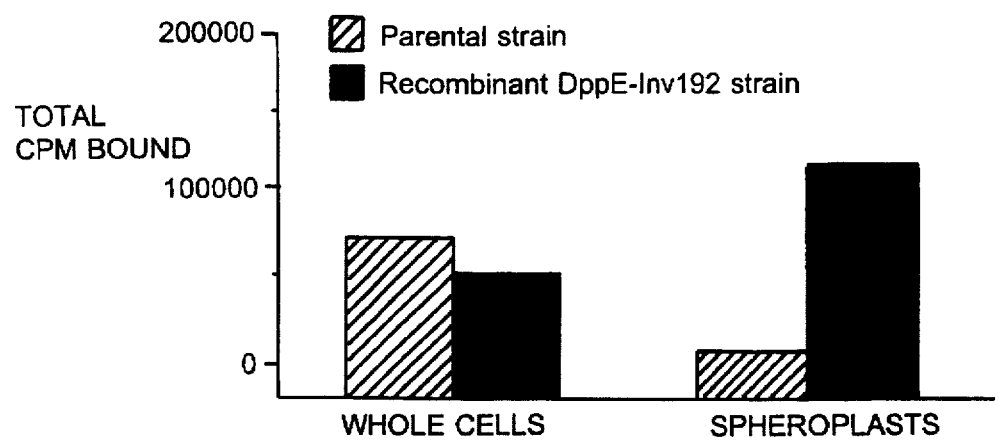
FIG. 3 is a bar graph showing results when whole cells or spheroplasts were incubated with iodinated monoclonal antibody 3A2-1 directed toward the C-terminus of Invasin. Bound counts were determined following washing.
Figure 2:
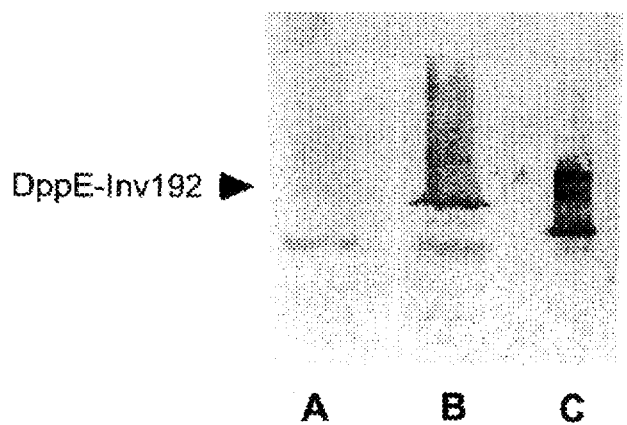
FIG. 2 is a blot showing a HEp-2 cell binding assay in parental (negative control) E. coli (Lane A), E. coli expressing DppE-Inv192 fusion protein (Lane B) and E. coli expressing the whole Invasin molecule (positive control) in Lane C.
Figure 4:
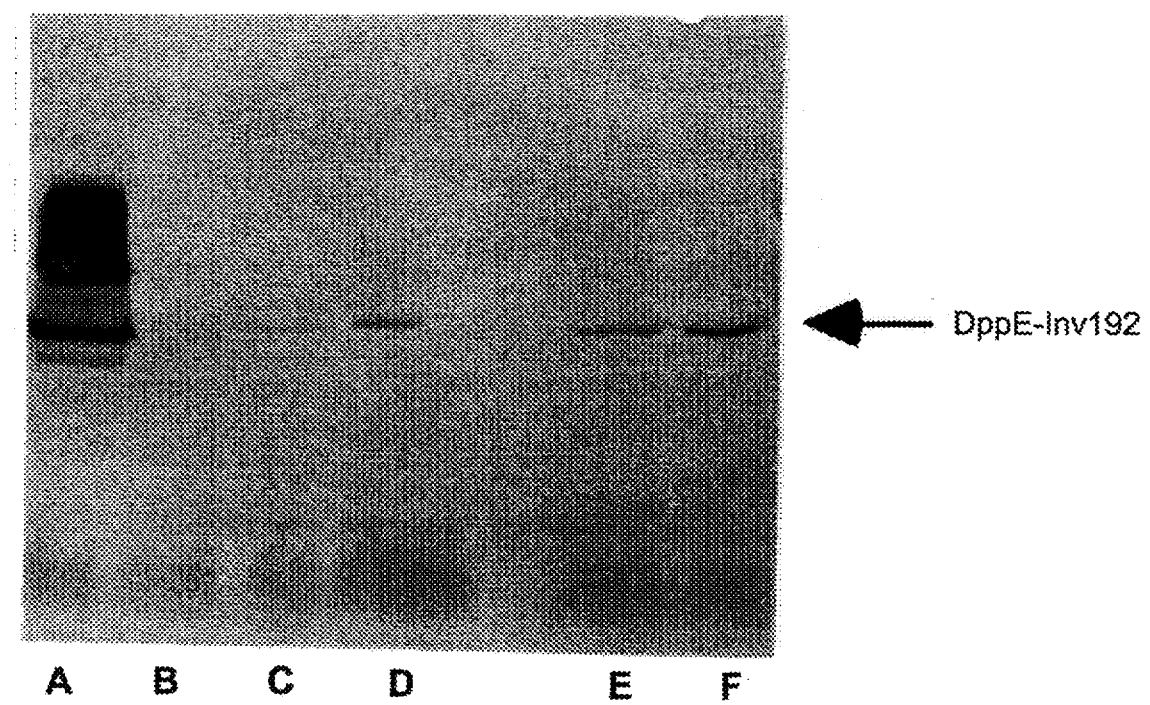
FIG. 4 is a Western blot of DppE-Inv192 expression in B. subtilis parental cells (lane B), recombinant spheroplast cytoplasm (lane C), recombinant spheroplast membranes (lane D), whole recombinant spheroplasts (lane E), and whole recombinant cells (lane F). Invasin expression in E. coli (positive control) is shown in lane A.
Figure 5:
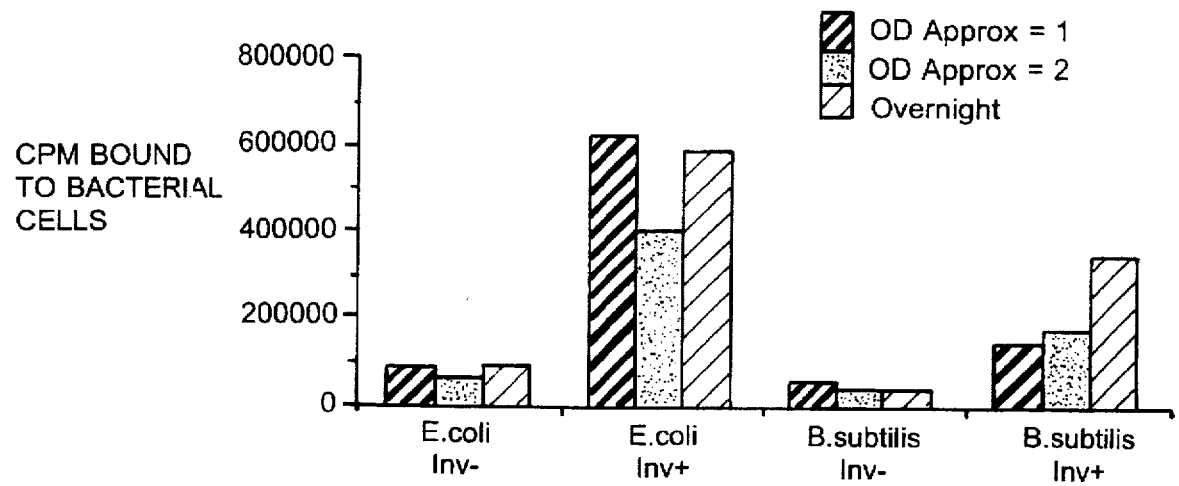
FIG. 5 is a graph showing whole cells from E. coli (with or without a plasmid coding for Invasin) or B. subtilis HJS31 (Inv −) and recombinant B. subtilis (CwbA-Inv192 +) incubated with iodinated 3A2-1. The total counts bound following washes are shown.

The invention provides heat and environmentally resistant multicomponent live vaccine vectors for oral administration. Bacterial spores are ideal because of their natural and unusually high resistance to heat, mechanical disruption, dryness, UV irradiation, chemicals and enzymes, such as lysozyme, and because of their very long shelf life under adverse conditions. An immune response is generated to specific antigens by enteral administration of spores from recombinant strains of spore forming bacteria, engineered either to express specific antigens on the spore surface, or to express antigens from the germinated vegetative cell, or a combination of both. Means to accomplish this include:

1. Expressing a variety of antigens as fusion proteins with, e.g., the B. subtilis CwbA vegetative cell wall protein, or using B. subtilis with the capacity to secrete antigenic proteins.

2. Expressing foreign antigens as fusion proteins with spore coat proteins in the spores of B. subtilis.

3. Utilizing other spore-forming organisms as an alternative antigen delivery system.

We have expressed foreign antigens from chromosomal inserts and plasmids in *B. subtilis*, and constructed and expressed fusion proteins in *B. subtilis*. Our data show that we can express portions of Invasin (a protein known to confer the ability to bind to mammalian cells when expressed on the surface of *E. coli*) on the surface of *B. subtilis* as a fusion protein with the cell wall protein CwbA. This invention provides a completely new concept of vaccine antigen delivery that could ultimately fulfill many of the requirements deemed necessary by the Children's Vaccine Initiative for the ideal vaccine delivery system.

One embodiment of the vaccine of the invention consists of bacterial spores engineered such that, following oral administration, the spores will germinate, allowing the resultant vegetative cells to colonize the gastrointestinal tract. The vegetative cells will then express one or more vaccine antigens of interest. It is preferable to establish at least transient gastrointestinal colonization with the vaccine strain. This may be achieved by using a spore-forming bacterium whose spore and/or vegetative form is naturally able to colonize the gastrointestinal tract to an extent sufficient to elicit an immune response. An alternative approach is to engineer a non-colonizing organism in such a way that it expresses colonizing factors on its surface (e.g., Invasin). In order for the colonizing organisms to deliver antigen within the gastrointestinal tract, the foreign protein can be expressed on the bacterial surface, or secreted by the colonizing bacteria.

Another embodiment is to use spores simply as inert carriers to deliver the antigens of interest, without necessarily requiring that they germinate. This concept is analogous in some respects to the use of microspheres containing specific antigens (Eldridge et al., *Curr. Top Microbiol. Immunol.*, 1989, 146:59–66; Moldoveanu et al., *J. Infect. Dis.*, 1993, 167:84–90). However, spores are much easier and cheaper to manufacture than are microspheres. Additionally, solvents are used in the preparation of microspheres, limiting the antigens which can be used in such a system. The spores of the invention have no such limitation. There are clear advantages to using spores destined to form vegetative cells in the gut in the production and delivery of vaccine antigens, since they will perpetuate (through colonization) and amplify (through cell division) the antigen.

In a third general embodiment, the two previous embodiments are combined: spores carry an antigen on the spore surface, exposing it to the animal, and the spores are also able to germinate and produce vegetative cells which express an antigen (on the surface or secreted). The antigen on the spore coat and the antigen expressed by the vegetative cell can be the same or different.

Alternative Vectors

Spore-forming bacteria other than *B. subtilis* can be used as vaccine vectors, including other members of the genus Bacillus. *B. subtilis* is able to grow at least to a limited extent in the absence of oxygen. Other Bacillus, e.g., *B. polymyxa*, are facultative anaerobes and grow vigorously in the absence of oxygen. *B. polymyxa* and *B. subtilis* have 44 and 43 Mol % G+C respectively (Priest, 1993, supra) and are considered to be closely related, so it is likely that the constructs developed in *B. subtilis* will also work in *B. polymyxa*.

Another group of organisms for use in the invention is the anaerobic spore-forming Clostridium, some of which readily colonize the gastrointestinal tract, and are adapted for survival in an anaerobic environment. Gene transfer technology has recently been developed for *C. perfringens* and *C. acetobutylicum*. *C. perfringens* would be suitable with regard to foreign antigen expression in vivo, because it forms spores and colonizes the gastrointestinal tract. To avoid the usual pathogenicity of many Clostridial species, one can use an attenuated strain of *C. perfringens* which does not produce human toxins. For example, perfringolysin O and phospholipase C mutants of *C. perfringens* have been constructed and shown to have altered virulence properties (Rood et al., *94th General Meeting of The Amer. Society for Microbiology*, 1994, D-73; hereby incorporated by reference). Precedents exist for attenuation of enteral pathogens (such as *V. cholerae* and Salmonella) and thus these organisms may be used for vaccine delivery. Another option is to use a nonpathogenic Clostridium which fulfills the criteria of spore formation and colonizing ability.

Delivery of Antigens

In order to demonstrate that spores can deliver foreign or recombinant antigens, we have shown that foreign antigens can be expressed on the surface of vegetative cells following germination of spores, and that several different antigens can be expressed by vegetative cells. Additionally, we have shown that oral administration of the recombinant spores results in the desired immune response.

To express antigens on the surface of the spores, one can take advantage of the special properties of spore coat proteins. Spore coats have two distinct layers, a thick, more dense outer coat and a less electron-dense inner coat (Setlow, "Spore structural proteins," In *Bacillus subtilis* and other Gram-positive Bacteria, Sonenshein et al., (eds.), Amer. Society for Microbiology, Washington D.C., 1993). Several of the coat protein genes (cot) have been sequenced and their regulation studied; however, any coat proteins can be used in the invention. Based on such information, it is possible to construct genetic fusions between inner or outer coat protein genes and a heterologous gene of interest in order to express antigens of interest as fusion proteins on spore coats.

Many different antigens can be delivered on spore coats, but it is also included in the scope of the invention to deliver antigens via vegetative cells, particularly of the genus Bacillus. Some vegetative bacterial cells can be transported without requiring cold storage, and can be administered without being induced to sporulate under certain conditions. Alternatively, the cells could be transported as spores and induced to germinate in vitro, the resulting vegetative cells being administered to the patient.

We have shown the feasibility of our invention by demonstrating that we can express foreign virulence genes in *B. subtilis* and direct *B. subtilis*-Yersinia fusion proteins to specific and predictable locations within *B. subtilis*.

Invasin is known to be a primary factor for mammalian cell invasion by *Y. enterocolitica* (Pepe et al., *Proc. Natl. Acad. Sci. USA*, 1993, 90:6473–77). It is also known to bind to multiple β1 chain integrins (Isberg et al., *Cell*, 1990, 60:861–71) which are present on M cells in the gastrointestinal tract. It is not unreasonable, therefore, to expect that if the spores or vegetative cells of the invention are able to bind to any portion of the gastrointestinal tract, and if Invasin is involved in that adhesion process, then the spores or vegetative cells will bind preferentially to M cells. The fate of the spores following their binding to M cells is likely to be internalization, and subsequent presentation to the lymphocytes within the M-cell pocket.

In order to determine the likelihood of a recombinant cell adhering to gastrointestinal cells, once a colonizing factorand/or antigen-bearing construct has been made and introduced into a bacterial vector, binding experiments are undertaken to determine the bacterial cell's adherence phenotype. This is done by adding vegetative bacterial cells or spores (which have been shown to express Invasin or other colonizing factors on their surface) to tissue culture cell monolayers. The monolayers are incubated for 3 hours and then washed extensively. The cells are then stained with Giemsa and examined by light microscopy. Inv(+) bacterial cells are compared with Inv(-) strains. It is possible to see gross differences in degree of bacteria-cell binding using this method. Depending on the number of bacterial cells bound, it is possible to quantitate the number of bacteria per tissue culture cell. There may be differences in bacterial binding seen in different cell types (e.g., intestinal cells). If there are no apparent quantitative differences in binding of the recombinant Bacillus to tissue culture cells, it is possible to examine the bacterial cell-tissue culture cell interactions using transmission electron microscopy in order to see if there is a qualitative difference between the parental and Inv(+) Bacillus binding to eukaryotic tissue culture cells. Bacterial vectors which bind well to the tissue culture cells may be good candidates for useful vaccines, since they are likely to enterically colonize the immunized animal at a higher rate and/or for a longer time.

In addition to the HEp-2 cells used in the following examples, other cell lines can be used for experiments to determine bacterial cell binding, e.g., gut derived CaCo2 and T84 cells. CaCo2 cells polarize, form tight junctions and a microvillus surface, and are analogous to a villus type cell. T84 cells also form a polarized monolayer, but are more analogous to crypt cells.

*Bacillus subtilis* was chosen for the experiments described herein for two primary reasons. First, it is the spore-forming organism about which most is known genetically, biochemically, and physiologically (Priest, "Systematics and Ecology of Bacillus," In *Bacillus subtilis and other Gram-positive Bacteria*, Sonenshein et al., (eds), Am. Society for Microbiology, Washington, D.C., 1993)). Second, *B. subtilis* is not a human pathogen. However, as mentioned above, any spore forming bacterium is a candidate for use in the invention.

Methods for expression of various exogenous proteins in *B. subtilis* are well-documented, e.g., *E. coli* β-galactosidase, diphtheria toxin, all five pertussis toxin subunits individually (Hemila et al., *FEMs Microbiol. Lett.*, 1989, 65:193–98; Saris et al., *FEMs Microbiol. Lett.*, 1990, 68:143–48; Runeberg-Nyman et al., *Microbiol. Path.*, 1987, 3:461–68), pneumolysin, and interferon (Palve et al., *Gene*, 1983, 22:229–35, Taira et al., *Gene*,1989,77:211–18; all hereby incorporated by reference).

There are several ways to determine where the expressed fusion proteins are situated in the spore coat or cell wall. One way is to determine if radiolabeled monoclonal antibody 3A2-1 (which is directed toward the C-terminal 192 amino acids of Invasin) is able to bind preferentially to the spores or vegetative cells (as we found with spheroplasts for the DppE-Invasin fusion protein, and for whole cells with the CwbA-Invl92 fusion protein). Another is to use indirect or direct fluorescence with either a FITC conjugated anti-murine antibody or fluoresceinating 3A2-1, respectively. It may be necessary to use ultrastructural morphological techniques to determine the site of the fusion protein in some cases, e.g., by using immunogold techniques with 3A2-1.

We have expressed proteins, such as Shiga-like toxin I B subunit (SLT-I B) and portions of Invasin from *Y.*

*pseudotuberculosis*, in *B. subtilis*. We have expressed SLT-I B from both plasmid and chromosomal sites within *B. subtilis* and clearly demonstrated the expressed protein in culture supernatants of the genetically altered *B. subtilis* cells. We have constructed genetic fusions between B. subtilis cell membrane or cell wall proteins and the carboxy-terminal domain of Invasin, and have expressed the resultant fusion proteins in *B. subtilis*. Our experiments established that it is possible to target a portion of Invasin to either the cell membrane or cell wall of *B. subtilis*, and that the fusion protein retains the phenotypic characteristics of Invasin, in terms of HEp-2 cell binding. Additionally, we have demonstrated that the CwbA-Inv fusion proteins are immunogenic when expressed from vegetative *B. subtilis* following oral administration of spores encoding the CwbA-Inv fusions.

METHODS AND EXAMPLES

The data and examples provided herein illustrate embodiments of the invention, and are not intended to be limiting.

I. Recombinant proteins secreted from and expressed on the surface of vegetative cells

Example 1: Expression of Shiga-like toxin I B subunit in *B. subtilis*

We have purified and characterized the Shiga-like toxins (SLTs) produced by enterohemorrhagic *E. coli* (Donohue-Rolfe et al., *Infection and Immunity*, 1989, 57:3888–93; Acheson et al., *J. Infectious Diseases*, 1990, 161:134–37; Acheson et al., *Amer. Society for Microbiology*, 1990, B206; Calderwood et al., *Infection and Immunity*, 1990, 58:2977–82; Acheson et al., *Infect. Immun.*, 1993, supra; Acheson et al., *Microb. Pathog.*, 1993, 14:57–66; Acheson et al., *Amer. Society for Microbiology*, 1993, B-98; all hereby incorporated by reference). This work was initially undertaken to develop purification schemes for the SLTs, but also resulted in the development of various ELISAs to detect both holotoxins and SLT B subunits (Acheson et al., *Infection and Immunity*, 1990, 161:134–37; Acheson et al., *Microb. Pathog.*, 1993, supra). We have cloned the genes for both SLT-I and-II B subunits into expression vectors which place them under the control of the T7 promoter. This has enabled us to metabolically label the two proteins separately and has also allowed us to purify SLT-II B subunit (Acheson et al., *Infect. Immun.*, 1995, 63:301–308).

We expressed Shiga-like toxin I B subunit in *B. subtilis* using the following methods. The SLT-I B subunit gene (sltIB) was removed from plasmid pSC4 (Calderwood et al., *Proc. Natl. Acad. Sci.*, 1987, 84:4364–68) as an SspI-BamHI fragment and cloned into the SspI and BamHI sites of pBluescript SK- to create pDA5. A HindIII-SacI fragment was then removed from pDA5 and cloned into pAF3 (Fouet et al., *J. Bacteriol.*, 1990, 172:835–44) to construct pDA1, in which sltB is under the control of the hybrid SPAC promoter that allows expression in both *E. coli* and *B. subtilis*. pAF3 contains an Amp$^r$ marker that is expressed in *E. coli* and a Cam$^r$ gene that is expressed in *B. subtilis*, but only replicates as an autonomous plasmid in *E. coli* (Fouet et al., supra). To express Cam$^r$ in *B. subtilis*, the DNA must integrate into the host cell chromosome. In pDA1, the DNA of interest (sltIB) is positioned between the carboxy and amino termini of the *B. subtilis* α-amylase gene (amyE). As a result, when pDA1 was linearized and introduced into *B. subtilis*, it was able to integrate into the host chromosome by double cross-over within the non-essential amyE gene. Colonies were then selected on the basis of Cam resistance and inability to make amylase.

While pDA1 did express SLT-I B subunit in *E. coli* DH5α (detectable both by ELISA and Western blot), very low levels were detected in *B. subtilis*. To increase expression in *B. subtilis*, the SPAC promoter was replaced with the *B. subtilis* glutamine synthetase promoter, a strong promoter regulated by the nitrogen source in the medium. Following integration of this next generation construct (pDA6) into the *B. subtilis* chromosome, B subunit expression was clearly demonstrated and was repressed upon the addition of glutamine (FIG. 1). The B subunit was secreted into the medium and none was detectable in the cell-associated fractions. Since the cloned sltB was translated from its natural initiation codon and includes a secretion signal sequence at its N-terminus, we assume that this sequence was recognized by the *B. subtilis* protein export machinery.

B subunit levels in the culture fluid fell after the cultures entered stationary phase due to protease activity. We were able to transiently delay the degradation of the B subunit by addition of phenylmethylsulfonyl fluoride (PMSF) to the culture medium.

In order to increase the level of B subunit expression further, we constructed plasmid pDA26, in which the glutamine synthetase promoter and the sltB gene were cloned in a high-copy plasmid. Cultures of *B. subtilis* carrying pDA26 produced about ten times more B subunit than did strains carrying only a single copy of the construct. As before, all the detectable SLT-I B subunit was in the culture fluid.

The ELISA for the detection of SLT-I B subunit is based on a monoclonal antibody capture system (Calderwood et al., 1990, supra; Acheson et al., 1993, supra), demonstrating that the B subunit produced by the *B. subtilis* strains is authentic. We were also able to show that the B subunit produced by *B. subtilis* was able to bind to hydatid cyst material in an ELISA, which is a capture system to both affinity-purify and quantitate SLTs (Acheson et al., *J. Infect. Dis.* 1990, supra; Calderwood et al., 1990, supra).

These experiments demonstrate that our constructs yielded a functional, secreted, heterologous protein in *B. subtilis.*

Example 2: Expression of Dpp Fusion Proteins in *B. subtilis*

In order to examine the expression of antigens of interest on the surface of *B. subtilis*, we took advantage of the special properties of the dipeptide permease (dpp; originally dciA) operon (Mathiopoulos et al., *Mol. Microbiol.*, 1991, 5:1903–13). The dpp operon is composed of a series of genes (dppA, dppB, dppC, dppD, dppE) involved in the uptake and transport of peptides.

The dppE gene encodes a dipeptide binding protein which is secreted from *B. subtilis* but remains attached to the membrane by a lipoprotein linkage. We hoped therefore that dppE would be exposed on the cell surface. The C-terminus of the dppE gene was fused in frame to DNA encoding the 192 C-terminal amino acids of Invasin from *Yersinia pseudotuberculosis*. This Invasin protein is a 103 kDa protein (986 amino acids) which has been shown to be localized in the outer membrane (Isberg et al., *Cell*, 1987, 50:769–78). The integrin binding domain of Invasin has been identified as being within the carboxyl-terminal 192 amino acids (Leong et al., *EMBO J.*, 1990, 9:1979–89). Thus, the C-terminal 192 amino acid portion of Invasin has the potential to cause bacterial cells on whose outer surface it is expressed to attach to mammalian cells.

To construct the DppE-Invasin fusion protein, we cloned the whole of the dppE gene, excluding the termination codon, using PCR. The primers were designed to have EcoRI and KpnI sites upstream, and a SacI site downstream to allow cloning into the EcoRI and SacI sites of pBluescript SK and to facilitate sequencing of the fusion gene. The dppE gene was then cloned as an EcoRI-SacI fragment into the EcoRI and SacI sites of pAFl (Fouet et al., 1990, supra). The glutamine synthetase promoter was cloned upstream of the dppE gene as an EcoRI-KpnI fragment. The nucleotides encoding the carboxy terminal 192 amino acids of Invasin were then amplified using PCR. SacI sites were appended to each end to allow in-frame insertion into the SacI site of the previously constructed plasmid. The result was a plasmid (pDA74) containing a fusion gene consisting of the whole of the dppE coding sequence and the portion of the carboxy terminus of Invasin which is responsible for binding to cells. The gene fusion was positioned between the amino and carboxy terminal portions of the amyE gene as before, to allow integration into the *B. subtilis* chromosome.

Expression of the DppE-Invasin fusion protein was demonstrated in *E. coli*. The fusion protein (approximately 80 kDa) was detected by Western blot using a monoclonal antibody (3A2-1) directed toward the C-terminus of Invasin (Leong et al., 1991, supra). We determined the ability of the fusion protein expressed in *E. coli* to bind HEp-2 cells by transferring the fusion protein onto nitrocellulose and then incubating the membrane with HEp-2 cells. Bound HEp-2 cells were detected by virtue of their endogenous alkaline phosphatase activity. HEp-2 cells bound to Invasin present in the positive control *E. coli* (FIG. 2, Lane C), and to the DppE-Inv192 fusion protein in lane B (FIG. 2). Non-specific binding can be seen in lanes A and B in a band just below the level of the DppE-Inv192 fusion protein (FIG. 2). pDA74 was then linearized and introduced into *B. subtilis*. The fusion protein was not only expressed in *B. subtilis* but was also able to bind HEp-2 cells, as determined by blotting.

In order to increase expression of the fusion protein, pDA74 was introduced into *B. subtilis* strain HJS31 (a glnR mutant) in which the glutamine synthetase promoter is expressed constitutively. The physical location of the fusion protein in the *B. subtilis* strain carrying the DppE-Inv192 fusion was determined using a variety of techniques. Binding of $^{125}$I-labeled monoclonal anti-Invasin antibody 3A2-1 to the fusion protein was confirmed by an autoradiograph of a Western blot. When binding to whole bacterial cells was tested, the iodinated antibody bound to both the parental and the DppE-Inv192 recombinant strain to approximately the same extent (FIG. 3). However, when binding to spheroplasts (prepared by incubating whole cells with lysozyme, and confirmed by microscopy) was determined, there was approximately 5-fold more binding of the antibody to the recombinant spheroplasts than to control spheroplasts (FIG. 3).

To further determine the location of the fusion protein, spheroplasts were diluted with water to induce lysis. Following lysis, the centrifugation pellet (containing spheroplast membranes) and supernatant (containing spheroplast cytoplasm) were examined by Western blot using 3A2-1. The fusion protein was readily detected in whole cells and spheroplasts and was clearly present in the spheroplast membranes. There was also some fusion protein present in the spheroplast cytoplasm which may be due to contaminating membranes (FIG. 4).

Overall, we conclude from these data that the fusion protein is expressed and that at least the Inv192 component is localized to the outer surface of the cytoplasmic membrane.

Example 3: Expression of *B. subtilis* Cell Wall Protein-Invasin Fusion

*B. subtilis* produces a number of cell wall proteins. Two of the best studied classes of cell wall proteins are the autolysins and their associated modifier proteins, which are thought to be important in regulating autolysin activity. Kuroda et al. (*J. Bacteriol.*, 1991, 173:7304–12) cloned and sequenced a major autolysin gene, designated cwlB. Kuroda et al. (1991, supra) subsequently sequenced a gene for a modifier protein, designated cwbA, which is immediately upstream of cwlB. We constructed a genetic fusion using the whole of cwbA and the DNA encoding the C-terminal 192 amino acids of Invasin. The cwbA gene encodes a polypeptide of 705 amino acids with a molecular mass of 76,725 Da (Kuroda et al., supra). In order to clone the cwbA gene, we designed PCR primers which annealed to the 5' end of the gene and included the ribosomal binding site. The reverse primer was designed to anneal to the downstream portion of the gene and to exclude the termination codon. The upstream primer contained a KpnI site and the downstream primer a SacI site. Following PCR, we obtained a 2140 bp fragment containing the cwbA gene, as expected. Following appropriate restriction digestion, the fragment was inserted into the KpnI and SacI sites of pBluescript SK. The 5' portion of the insert was sequenced to check that it was the correct gene. The next stage of the construction involved moving the KpnI-SacI fragment from the pBluescript vector into plasmid pDA74 (described above) which placed the cell wall protein gene under the glutamine synthetase promoter. Next, the DNA encoding the terminal 192 amino acids of Invasin was amplified using PCR primers with SacI restriction sites on each end. The PCR product was inserted downstream of and in-frame with cwbA. The fusion site was sequenced and the final plasmid containing the cwbA-inv192 gene fusion was designated pDA84. The gene fusion was integrated into the amyE locus of *B. subtilis* HJS31. This strain produced detectable levels of the fusion protein (by Western blot with monoclonal antibody 3A2-1). The size of the reactive band was about 100 kDa, as expected.

When *B. subtilis* expressing the CwbA-Inv192 fusion protein was grown to early stationary phase and the cells treated with lysozyme in the presence of 0.5M sucrose to maintain the spheroplasts, there was clearly more CwbA-Invasin protein, as a proportion of the total protein, in the lysozymal supernatant than in the spheroplasts. Thus it appeared that the CwbA-Invasin protein was predominantly associated with the cell wall. When we examined the binding of iodinated 3A2-1 to *B. subtilis* HJS31 and the recombinant CwbA-Inv192 expressing *B. subtilis* at three different points in their growth curve, there was a clear difference in the binding of the monoclonal antibody to the two strains (FIG. 5). There was a similar difference when the same experiment was performed with *E. coli* which did and did not express Invasin (FIG. 5). The same number of bacterial cells was used at each growth point, and the ratio of binding in overnight cultures between Invasin positive and negative *B. subtilis* (8.1) and *E. coli* (6.0) was similar. There was some suggestion that the binding of 3A2-1 to the Inv(+) Bacillus increased as the cultures grew, since the binding to control HJS31 did not really change during the course of the culture.

The binding of iodinated monoclonal antibody to spheroplasts was then assessed. Whole cells and spheroplasts of *B. subtilis* HJS31 and the recombinant B. subtilis, which had been grown to an optical density (600 nm) of approximately 1.0, were incubated with iodinated 3A2-1 and the bound counts compared. As shown in Table 1, the ratio of bound counts between the two strains suggested that removing the cell wall also eliminated most of the preferential binding of 3A2-1.

TABLE 1

Comparison of CPM bound to whole cells and spheroplasts in *B. subtilis* HJS31 (Inv −) and the recombinant strain (Inv +).

| | CPM bound to whole cells | CPM bound to spheroplasts |
|---|---|---|
| HJS31 (Inv −) | 77925 | 52712 |
| Recombinant (Inv +) | 162589 | 41495 |
| Ratio | 2.1 | 0.8 |

Whole cell extracts of CwbA-Inv192 expressing *B. subtilis* were able to bind HEp-2 cells on a blot, as described above for the DppE-Inv192 expressing strain.

Spores of the CwbA-Inv192 expressing recombinant strain were prepared by growing the cells in DS medium for 48 hours. The spores were washed 3 times in sterile deionized water. Spores were kept for two weeks in water and then an aliquot germinated by incubating the spores overnight in Luria Bertani medium. The resulting bacterial cells were harvested and found to be expressing CwbA-Inv192 by Western blots. This confirms that the spores retain the capacity to germinate into vegetative cells which express recombinant fusions proteins.

Expression of Larger Pieces of Invasin on the Surface of *B. subtilis*

Additional cwbA-inv gene fusions were made using PCR as described for the original construction of cwbA-inv192. There are no SacI sites in the inv gene, but cassettes containing different amounts of inv with SacI sites appended to each end were made to allow the new inv DNA to be moved directly into the SacI site of pDA84, which resulted in an in-frame insertion of inv DNA without having to alter the rest of the construct. We cloned DNA segments encoding the C-terminal 292 amino acids, the C-terminal 497 amino acids, and the C-terminal 780 amino acids (Leong et al., 1991, *Infect. Immun.*, 59:3424–33; Rankin et al., 1992, Infect. Immun., 60:3909–12). *B. subtilis* transfected with these constructs showed expression of the different sizes of fusion proteins.

Should it be necessary to enhance the invasive phenotype of the bacterial cells, greater amounts of the CwbA-Invasin fusion proteins can be expressed on the cell surface by using a stronger promoter, or alternatively, by making fusions with other cell wall or cell wall modifier proteins as well as with CwbA.

II. Fate and Immunogenicity of Recombinant Spores and Vegetative Cells Following Oral Administration Experiments were conducted in mice to determine the fate of recombinant *B. subtilis* vegetative cells and spores following oral inoculation and to investigate the ability of the recombinant vegetative cells and spores to induce an immune response following either parenteral or oral administration.

Example 4: The Fate of *B. subtilis* Spores Administered Orally to Mice

Groups of 2–5 Swiss Webster mice were given either $10^7$ vegetative cells grown to mid-log phase or $10^{10}$ spores of *B. subtilis* strain JH642 containing the integrated sltIB construct (which contains a chloramphenicol resistance marker, and is an auxotroph for phenylalanine and tryptophan) by oral gavage using a feeding needle. Single animals were then sacrificed at intervals (up to 10 days) and their entire gastrointestinal tracts removed and divided into four components (stomach, small bowel, cecum and large bowel). Each section of the gut was rinsed with 2 ml of phosphate Allowing for the inherent inaccuracies of the experimental methods, there was reasonable agreement between the pairs of mice at each time point. Although spores containing recombinant DNA were recoverable from the GI tract up to 7 days, there was a significant drop in the number of recoverable spores after the first day.

TABLE 2

| Days after Inoculation | Stomach | | Small bowel | | Cecum | | Large Bowel | | Lungs |
|---|---|---|---|---|---|---|---|---|---|
| | Total | Spores | Total | Spores | Total | Spores | Total | Spores | Total |
| 1 Mouse 1 | >$10^5$ | >$10^5$ | >$10^5$ | >$10^5$ | >$10^5$ | >$10^5$ | >$10^5$ | >$10^5$ | <40 |
| 1 Mouse 2 | 11100 | 13600 | 1750 | 3000 | 15100 | 14000 | >$10^5$ | >$10^5$ | <40 |
| 2 Mouse 3 | C | 2100 | C | 7500 | C | 4500 | C | 10800 | >$10^5$ |
| 2 Mouse 4 | C | 2300 | C | 400 | C | 400 | C | 320 | <40 |
| 5 Mouse 5 | <40 | 80 | 80 | 80 | 40 | 40 | 40 | <40 | <40 |
| 5 Mouse 6 | 40 | <40 | <40 | <40 | 40 | <40 | 40 | 40 | <40 |
| 7 Mouse 7 | <40 | <40 | <40 | 40 | 40 | 40 | 40 | 40 | <40 |
| 7 Mouse 8 | <40 | 80 | <40 | <40 | 560 | 600 | 400 | 440 | 80 |

Table 2 The numbers of organisms recovered from the 2 ml gut washings and lung homogenate are shown. Total cells represents CFUs from samples which were not heated (80° C. 20 min) compared with spores which were heated. The "total" plates from Day 2 were heavily contaminated (C) by non-Bacillus species and it was not possible to count the number of Bacillus.

buffered saline (PBS) and 100 µl plated onto DS medium containing chloramphenicol. The combination of high salt media, aerobic culture and chloramphenicol prevented growth of almost all the naturally occurring enteric bacteria. Colonies were deemed to be *B. subtilis* by virtue of colony morphology, resistance to chloramphenicol, and in selected cases, determining that they were auxotrophic for phenylalanine and tryptophan. The results from these experiments in mice showed that very low numbers of viable bacteria were detectable up to two days following administration of vegetative cells. Following administration of spores, however, we were able to recover colony forming units (CFUs) throughout the gastrointestinal tract up to 10 days following gavage. The apparent difference in survival of spores and vegetative cells may be due in part to the different inoculum sizes used.

To see if the mice were reinfecting themselves by coprophagia, the animals were fed spores and then placed in cages with raised floors to allow fecal matter to fall through. Despite these maneuvers we were still able to culture the starting strain of *B. subtilis* from each segment of the GI tract up to at least 6 days post-gavage. The CFUs originated from spores, since they survived heating (80° C. for 20 minutes) prior to plating.

Further experiments were undertaken by feeding eight mice with $10^{10}$ spores from the recombinant CwbA-Inv192 strain using a feeding needle. The animals were sacrificed at various times and the gastrointestinal tract processed as described above. The volume of fluid added to each gut segment was exactly 2 ml and 50 µl of this mixture was then plated on DSM plates containing 2.5 µg/ml chloramphenicol. The total number of *B. subtilis* per 2 ml of original solution was calculated by multiplying the final CFUs by 40. This calculation does not take into account any organisms which may have remained attached to the gut epithelial cells. The lungs were also removed, mixed with PBS, homogenized, and an aliquot plated for colony counts. Aliquots of gut contents were heat treated (80° C. for 20 min) to determine the ratio of vegetative cells to spores. The data from these experiments are shown in Table 2.

Figure 6:
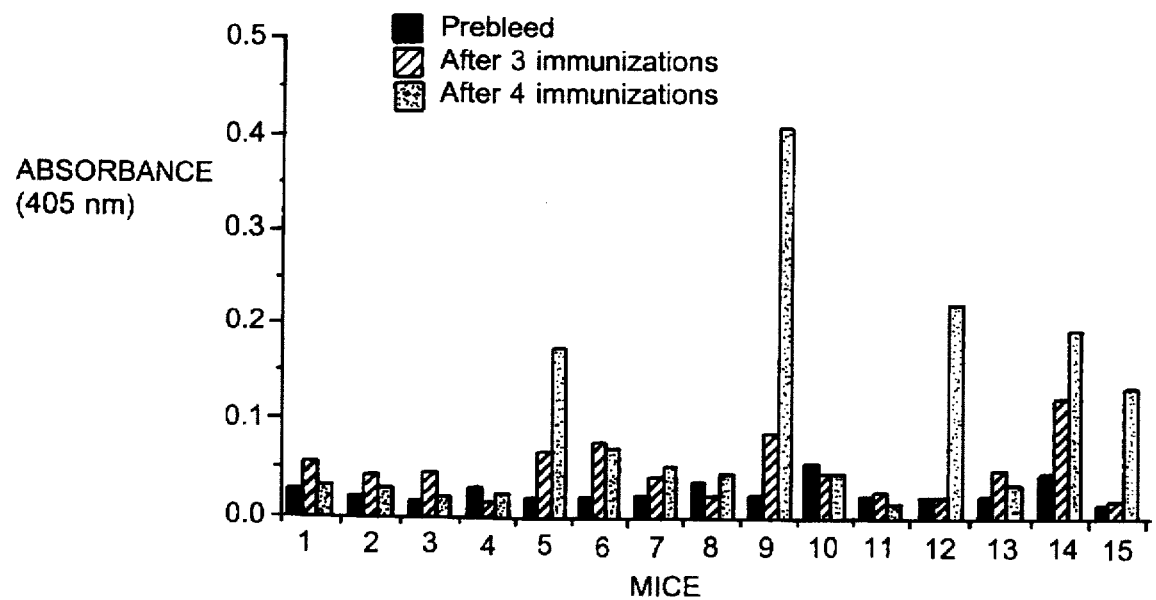
FIG. 6 is a graph showing binding of murine antibodies to Invasin in an ELISA from 15 mice orally immunized with spores whose vegetative cells expressed CwbA-Inv fusion proteins. The results are expressed as absorbance units (405 nm).

Example 5: Evaluation of Immune Response to Oral Vaccination by Spores or Vegetative Cells To determine whether or not the otherwise unmodified spores of *B. subtilis* containing the DNA encoding the CwbA-Inv fusion proteins could induce an immune response in vivo, spores were administered orally, directly into the stomachs, of 19 mice using a gavage needle. Each mouse received four doses of $1\times10^{10}$ spores at 10 day intervals. Animals were bled prior to the experiment (for control serum) and 10 days after the third and fourth inocula. The presence of IgG serum antibodies to Invasin was measured using an ELISA format with recombinant Invasin as the capture molecule. Five of the mice developed serum antibodies to Invasin with an increasing titer after multiple immunizations (FIG. 6). The antibodies detected by ELISA were also functional and able to neutralize Invasin, in that they were able to inhibit invasion by Inv-positive *E. coli* into mammalian HEp-2 cells.

We know that the spores themselves do not express the Invasin protein, and therefore the only way these mice could develop an immune response to Invasin is if the spores germinate and express the fusion antigen. In these experiments, we did nothing to optimize colonization and survival of the vector in the gastrointestinal tract. It is possible that prolonged recycling of spores could occur by coprophagy, typical in mice. However, this would not produce a specific antibody response without germination and expression of the protein antigen.

The data from Examples 1–5 show that the SLT-I B subunit can be expressed in *B. subtilis* and that this protein is exported from the cell, presumably by virtue of its own signal peptide. These experiments show that it is possible to construct and express two different fusion proteins (using in this case the C-terminus of Invasin) directed toward either the cell membrane or the cell wall of Bacillus. The experiments also show that *B. subtilis* vegetative cells are able to survive in the GI tract of mice at least two days following oral gavage. This indicates survivability of the cells, one of the requirements of our vaccine constructs. We also demonstrate that spores can be recovered to at least 7 days post-gavage, which is clearly longer than the GI transit time, and our data show that following oral immunization with spores, germination can occur within the gastrointestinal tract and the resulting vegetative cells can express the inv fusion gene in sufficient quantities to result in a systemic immune response.

III. Expressing Functional Antigens as Fusion Proteins with Spore Coat Proteins In this embodiment, a functionally active Invasin protein is expressed on the surface of B. subtilis spores. The experiments outlined above will determine which portion of Invasin is the best to use to confer Invasin functional activity. Invasin can be fused to a variety of cot genes to facilitate adherence to eukaryotic cells.

Construction of Gene Fusions Between Cot Genes and Antigens

Below are described specific strategies for constructing appropriate spore coat antigens. One skilled in the art will recognize that there are many protocols, promoters, vectors, etc., which will work in this invention. Therefore, the following descriptions and examples using cot and inv gene constructs are for illustrative purposes only and are not intended to be limiting. Antigens of interest are expressed on the spore coat by constructing gene fusions between known spore coat protein genes and the gene encoding the portion of Invasin shown to be the most appropriate in specific vegetative cells for conferring an invasive phenotype. Spores seem to form readily in the absence of any one of the coat proteins except CotE, so they are likely candidates for antigenic fusion proteins.

Antigenic epitopes of gene fusions between Inv epitopes and inner spore coat proteins may become buried within the structure of the spore, and so fusions to the inner spore coat may not be displayed on the outer surface of the spore. However, the advantage of using the inner coat is that the outer coat may offer some degree of protection to the fusion antigens. It may then be possible to make the outer coat fragile by heat treatment, thereby allowing coat dissociation and exposure of the antigen in the presence of gastric acid, while remaining intact for the purposes of stability and transport. It should be noted that virtually all the cot genes can be tested rapidly and easily, since the above-described cloning vector accepts any PCR product as a cassette.

It is necessary to place the cot-inv gene fusions under a promoter which will allow expression at an appropriate time and in an appropriate cellular compartment for incorporation of the fusion protein into the spore coat. Likely constructs are cot-inv fusions with cotC, which encodes a 12 kDa protein that is a major species of the outer coat, and cotD, which encodes an 11 kDa protein and is thought to be a major species of the inner coat (Setlow, 1993, supra; Donovan et al., 1987, supra).

The strategy described above, used for constructing the cwbA-invl92 gene fusion (using PCR) can be employed. The genes for cotA, -B, -C, -D, and -F have been sequenced (Donovan, et al., 1987, supra; Cutting et al., *J. Bacteriol.*, 1991, supra), allowing appropriate primer design for PCR to amplify the cot gene of interest with its promoter (using primers with overhanging restriction sites to allow cloning of the cot genes into pBluescript). The termination codon of the cot gene is deleted. The inv gene is then amplified using PCR and inserted in frame and downstream of the C-terminus of the cot gene. The termination codon of inv is retained. These constructs can then be cloned in pAF1. pAF1 contains an $Amp^r$ marker that is expressed in *E. coli* and a $Cam^r$ gene that is expressed in *B. subtilis*, but only replicates as an autonomous plasmid in *E. coli* (Fouet et al., J. Bacteriol., 1990, 172:835–44). To express $Cam^r$ in *B. subtilis*, the DNA must integrate into the host cell chromosome. In the described cot-inv gene fusion the DNA will be positioned between the carboxy and amino termini of the *B. subtilis* amyE gene. As a result, when the plasmids are linearized and introduced into *B. subtilis*, they will be able to integrate into the host chromosome by double cross-over within the nonessential amylase gene. Colonies are then selected on the basis of chloramphenicol resistance and inability to make amylase. After culture to form spores, it can be determined if the fusion protein has incorporated into the spore coat.

Alternatively, the cot-inv fusion cloned without a promoter or amyE segments can be used to transform *B. subtilis* directly. Single crossover recombination at the cot locus will place the fusion under normal cot gene regulation.

If the Inv portion which is optimal for vegetative cells in a CwbA fusion is not optimal in Cot fusions (e.g., spore coats), different pieces of Inv can be fused to Cot proteins.

IV. Other Spore-forming Organisms as an Alternative Antigen Delivery System

As stated previously, it is likely that spores from any bacterium will fulfill the requirements of an inanimate antigen delivery vehicle in this invention. However, we consider using a vegetative cycle as part of the antigen delivery network to be the optimal system. A primary consideration is that the vector should be safe to administer. Additionally, the organism must survive and colonize the gastrointestinal tract at least to a limited extent. Although *B. subtilis* survives adequately in the gastrointestinal tract, there are other options using different organisms, e.g., *B. polymyxa* and *C. perfringens*.

Example 6: Expression of Foreign Antigens in Recombinant *Clostridium perfringens*

DNA encoding the *C. perfringens* enterotoxin (cpe) promoter was removed from pSM100 (Melville et al., 1994, *Infect. Immun.* 62:5550–58) using PCR. We appended a PstI site to the uptstream primer and NdeI and ClaI sites to the downstream primer. The PCR fragment was digested with PstI and ClaI and inserted into the PstI and ClaI sites of pBluescript SK to construct pDA92. The SLT-IB subunit was removed from a B subunit-containing plasmid using primers with an NdeI site appended to the upstream primer and a KpnI site appended to the downstream primer. The PCR fragment was digested with NdeI and KpnI and inserted into the NdeI and KpnI sites of pDA92 to construct pDA93. pDA93 was then digested with PstI and KpnI, and the fragment containing the cpe promoter and SLT-I B gene inserted into the PstI and KpnI sites of pJIR750 (Bannam et al., 1993, *Plasmid* 229:233–235). This final plasmid (pDA94) was transferred into *C. perfringens* strain ATCC 3624 by electroporation (Steven Melville, personal communication). SLT-I B subunit was expressed from the recombinant *C. perfringens* strain and was detectable in the culture supernatant by ELISA, demonstrating that it is feasible to express foreign antigens in the enteric colonizing, spore forming *C. perfringens*.

V. Administration of Vaccines

The spores and cells of the invention may be administered by any means known in the art. For example, antigen encoding spores can be suspended in hot water or broth and cooled for oral administration to patients, a treatment which will encourage germination of the spores. Alternatively, the spores may be encapsulated or congealed in a suitable matrix as an oral tablet or capsule, using any known method (e.g., as found in Remington's Pharmaceutical Sciences, 18th edition, A. Osol, (ed.), Mack Publishing Co., Easton, Penn., 1990).

A particularly useful carrier may be particulate hydroxylated calcium phosphate (HCP), which may transport the adhering spores across the intestinal epithelium. This carrier can raise a poly Ig immune response, especially when transported across specialized enteric epithelium containing M cells. A preferred form of hydroxylated calcium phosphate is hydroxyapatite, a commercially available crystalline hydroxylated calcium phosphate ($Ca_{10}(PO_4)_6(OH)_2$).

Based on the dosage and course of treatment that showed successful enteric colonization of bacteria and elicited an immune response in the mouse model, a preferred range of dosage would be $10^7$ to $10^{13}$ spores per dose and 1–8 doses, preferably 1–4 doses, more preferably a single dose. If doses in this range are not sufficient, the number of spores per dose may be increased. Those skilled in the art will recognize the appropriate dosage level to test, from research reported herein and for other oral vaccines. Without intending any limitation as to course of treatment, the vaccine could be administered over 1–8 doses for a primary immunization schedule over one month as in Boedeker (*Amer. Gasteroenterological Assoc.,* 888:A-222, 1993).

Initiating Germination of Spores Prior to Oral Inoculation

Spore germination is a discrete, controllable process by which spores re-establish metabolic activity without grossly altering their structure. It is a prerequisite for the return to vegetative growth. In order to germinate, spores must first be activated either by aging or, more conveniently, by heat treatment. Activation makes the spores permeable to specific germinants. Spores pre-germinated prior to administration would retain surface proteins, allowing binding to targeted receptors in the GI tract, and also grow out to vegetative cells efficiently. Spores of *B. subtilis* have two major germinant systems: either L-alanine or a mixture of glucose, fructose, asparagine and KCl (GFAK) (Foster et al., *Mol. Microbiol.,* 1990, 4:137–41). Spores can be treated with heat shock and L-alanine or GFAK and then fed to the animal to be immunized. As a practical note for consideration in relation to administration of stored spores to humans in the field, it is possible to provide a dose of germinated spores by simply adding dormant spores to a hot broth such as beef bouillon, and allowing the broth to cool to an acceptable temperature before having the patient drink the solution.

Advantages of the Invention

The invention provides a means of presenting foreign antigens for vaccine purposes using a live, heat-stable vector to be administered orally. Although there exist many methods for vaccine delivery, none use orally administered vectors which are both heat stable and live. The advantages of this system primarily relate to the fact that spores are heat resistant and therefore do not require the use of refrigeration for either transport or storage. Therefore, vaccines made according to the invention will have a prolonged shelf life, significantly longer than that of other vaccines, independent of cold chain.

Novel features of the invention include the use of a spore for oral delivery of vaccine antigens; having the spore germinate in the gastrointestinal tract and present foreign antigens (the spore itself may also present antigens); and the fusion proteins described for use in the invention. There is expected to be a wide commercial application for the vaccines of the invention, since they will be inexpensive to produce, transport, store, and administer.

Other embodiments are within the following claims.

What is claimed is:

1. A method of stimulating an immune response to an antigen in a vertebrate animal, said method comprising:

a) providing a bacterial spore genetically engineered with DNA encoding said antigen and DNA encoding an invasin, and b) orally administering said bacterial spore to said animal so that said spore germinates producing vegatative bacteria and said antigen is expressed by said vegatative bacteria for presentation to the immune system of said animal, wherein said invasin is expressed on the surface of said vegatative bacteria so that said vegatative bacteria adhere to cells of said animal.

2. A method of stimulating an immune response to an antigen in a vertebrate animal, said method comprising:

a) providing a bacterial spore genetically engineered with DNA encoding said antigen and DNA encoding an invasin, wherein said antigen is expressed on the surface of said spore, and b) orally administering said bacterial spore to said animal so that said spore is presented to the immune system of said animal, wherein said invasin is expressed on the surface said bacterial spore so that said bacterial spore adheres to cells of said animal.

3. The method of claim 1 or 2 wherein said bacterial spore is of the genus selected from the group consisting of Clostridium, Actinomyces, Streptomyces, Nocardia, and Bacillus.

4. The method of claim 2, wherein said antigen is expressed in the cell wall of said bacteria.

5. The method of claim 1, wherein said antigen is expressed in the cell membrane of said bacteria.

6. The method of claim 1 wherein said vegatative bacteria colonize the gastrointestinal tract.

7. The method of claim 1 wherein said antigen is secreted by said vegatative bacteria.

8. The method of claim 1 or 2 wherein prior to oral administration said spores are treated to initiate germination.

9. The method of claim 8 wherein said treatment comprises heat treatment.

* * * * *